United States Patent [19]

Zerby et al.

[11] Patent Number: 5,451,401

[45] Date of Patent: Sep. 19, 1995

[54] DIPHOSPHONIC ACID ESTERS AS TARTAR CONTROL AGENTS

[75] Inventors: Kim W. Zerby; Jeffrey C. Hayes, both of Cincinnati, Ohio

[73] Assignee: The Procter & Gamble Company, Cincinnati, Ohio

[21] Appl. No.: 129,567

[22] Filed: Sep. 29, 1993

[51] Int. Cl.[6] .......................... C07F 9/40; A61K 7/16; A61K 7/26; C07C 35/12

[52] U.S. Cl. .......................... 424/57; 424/48; 424/49; 424/58; 424/195.1; 426/650; 426/534; 426/538; 514/108; 514/510; 514/901; 514/974; 558/158; 558/160; 558/161; 131/274; 131/275; 131/276

[58] Field of Search ............... 558/158, 160, 161; 426/538; 424/49-58

[56] References Cited

U.S. PATENT DOCUMENTS

| | | | |
|---|---|---|---|
| 2,946,725 | 7/1960 | Norris et al. | 167/93 |
| 3,070,510 | 12/1962 | Cooley et al. | 424/52 |
| 3,488,419 | 1/1970 | McCune et al. | 424/49 |
| 3,549,662 | 12/1970 | Imai et al. | 260/345.5 |
| 3,629,477 | 12/1971 | Model et al. | 424/340 |
| 3,678,154 | 7/1972 | Widder et al. | 424/52 |
| 3,737,522 | 6/1973 | Francis | 424/49 |
| 3,903,297 | 9/1975 | Robert | 424/305 |
| 3,941,772 | 3/1976 | Ploger et al. | 260/239 |
| 4,033,994 | 7/1977 | Watson et al. | 426/538 |
| 4,051,234 | 9/1977 | Gieske et al. | 424/52 |
| 4,083,955 | 4/1978 | Grabenstetter et al. | 424/49 |
| 4,136,163 | 1/1979 | Watson et al. | 424/54 |
| 4,197,316 | 4/1980 | Yu et al. | 424/317 |
| 4,208,401 | 6/1980 | Bauman | 424/54 |
| 4,294,852 | 10/1981 | Wildnauer et al. | 424/317 |
| 4,346,023 | 8/1982 | Buchl et al. | 426/538 |
| 4,350,645 | 9/1982 | Kurosaki et al. | 260/978 |
| 4,371,471 | 2/1983 | de Soyres et al. | 260/438.5 R |
| 4,375,001 | 2/1983 | Schenk | 426/538 |
| 4,459,425 | 7/1984 | Amano et al. | 568/666 |
| 4,472,373 | 9/1984 | Ryan | 424/54 |
| 4,619,934 | 10/1986 | Sunshine et al. | 514/277 |
| 4,663,154 | 5/1987 | Ryan | 424/54 |
| 4,736,051 | 4/1988 | Wakatsuki et al. | 558/105 |
| 4,783,465 | 11/1988 | Sunshine et al. | 514/255 |
| 4,894,220 | 1/1990 | Nabi et al. | 424/52 |
| 4,906,456 | 3/1990 | Gaffar et al. | 424/52 |
| 4,906,488 | 3/1990 | Pera | 426/573 |
| 4,980,153 | 12/1990 | Jackson et al. | 424/52 |
| 4,997,640 | 3/1991 | Bird et al. | 424/52 |
| 5,004,597 | 4/1991 | Majeti et al. | 424/52 |
| 5,260,051 | 11/1993 | Cho | 424/57 |

FOREIGN PATENT DOCUMENTS

| | | | |
|---|---|---|---|
| 0961412 | 1/1975 | Canada | 167/316 |
| 0161898 | 11/1985 | European Pat. Off. | A61K 7/16 |
| 0186405 | 7/1986 | European Pat. Off. | A61K 31/675 |
| 0278744 | 8/1988 | European Pat. Off. | A61K 7/16 |
| 310299 | 4/1989 | European Pat. Off. | |
| 321233 | 6/1989 | European Pat. Off. | |
| 354322 | 2/1990 | European Pat. Off. | |
| 537008 | 4/1993 | European Pat. Off. | |
| 541037 | 5/1993 | European Pat. Off. | |
| 0555864A1 | 8/1993 | European Pat. Off. | A61K 7/16 |
| 4118-M | 1/1965 | France | |
| 1924085 | 1/1970 | Germany | |
| 46-31559 | 9/1971 | Japan | |
| 2-1402 | 1/1990 | Japan | |
| 2-292210 | 12/1990 | Japan | A61K 7/16 |
| 1592011 | 7/1981 | United Kingdom | A01N 31/14 |
| WO92/17164 | 10/1992 | WIPO | A61K 9/20 |
| 9324498 | 12/1993 | WIPO | |

OTHER PUBLICATIONS

Davison et al J. Org. Chem. 51(25):4768-4779 (1986) "Phosphorylation of Isoprenoid Alcohols".

(List continued on next page.)

*Primary Examiner*—Shep K. Rose
*Attorney, Agent, or Firm*—Mary Catherine Poland; Kathleen M. Harleston; Douglas C. Mohl

[57] ABSTRACT

Polyphosphonic acid ester compounds with flavorant, coolant and/or sweetener components, and tartar, plaque and/or calculus control compositions with improved taste comprising one or more polyphosphonic acid ester compounds are described.

6 Claims, No Drawings

OTHER PUBLICATIONS

Jabloner et al J. Polym. Sci. Polym. Chem. Ed. 18(10):2933–2940 (1980) "Flavor Synthesis I. Menthol Esters".

Cremlyn et al Phosphorus and Sulfur 5:1–3 (1978) "Some Derivatives of 4-t-Butyloyclohexyl and 1-Menthol Phosphoro Chloridates".

Ramirez et al JACS 97:7181–7182 (1975) and JACS 98:5310–5319 (1976).

Thuong et al Bull. Soc. Chem. FR: 667–671 (1974).

Liao, Ming-Long and Seib, Paul A., "A Stable Form of Vitamin C: L-Ascorbate 2-Triphosphate. Synthesis, Isolation, and Properties", J. Agric. Food Chem., vol. 38, No. 2, 1990, 355–66.

Feldmann, Walter, "Das Trimetaphosphat als Triphosphorylierungsmittel fur Alkohole und Kohlenhydrate in waBriger Losung. Seine Sonderstellung unter den kondensierten Phosphaten", Chem. Ber. 100 (1967), 3850–60 (translation attached).

Imokawa, Genji, Ph.D., "Functions and Effects of Monoalkyl Phosphates (MAP) [Monoarukiru Rinsanen (MAP) no Kino to Sayo]", Fragrance Journal, 68, 21–28, 1984.

Miglani, D. C., E. Raghupathy, A. Rajasekher and S. Shyamala, "Studies on Salivary Phosphatases III, On the Possible Relation Between Salivary Alkaline Phosphatase Activity and Gingival Inflammation," J. Periodontol, Jul. 1974, 45(7), 511–13.

Kamat, N. V., "Biochemical Aspects of Periodontal Diseases: II. The Possible Significance of Calcium Phosphorus and Alkaline Phosphatase in Human Saliva," Journal Indian Dent. Asso. 50, 171–175, 1978 (month not known).

Saxton, C. A., B. Svatun and A. M. Lloyd, "Antiplaque Effects and Mode of Action of a Combination of Zinc Citrate and a Nonionic Antimicrobial Agent", Scand. J. Dent. Res. Jun. 1988, 96:212–7.

Jenkins, S., M. Addy and R. Newcombe, "Studies on the Effect of Toothpaste Rinses on Plaque Regrowth. (II). Triclosan With & Without Zinc Citrate Formulations," J. Clin. Periodontol, Jul. 1989, 16(6), 385–7 (Eng).

"A Better Way to Make the Medicine Go Down", Research News, Science, vol. 253, Sep. 6, 1991, pp. 1095–1096.

Jenkins, S., M. Addy and R. Newcombe, "Triclosan and Sodium Lauryl Sulphate Mouthrinses (II). Effects of 4–Day Plaque Regrowth", J. Clin. Periodontol Feb. 1991; 18: 145–48.

Marsh, P. D., "Dentifrices Containing New Agents For the Control of Plaque and Gingivitis: Microbiological Aspects," J. Clin. Periodontol, Jul. 1991, 18:462–67.

Lindhe, J., "Triclosan/copolymer/fluoride dentifrices: A new technology for the prevention of plaque, calculus, gingivitis and caries", Am. J. Dent., 3:S1–S72 (Sep. 1990).

Van der Ouderaa, F. J. and Cummins, D., "Delivery Systems for Agents in Supra– and Sub-gingival Control", J. Dent. Res., 68:1617–24 (Nov. 1989).

King, Robert E., PhD., "Tablets, Capsules, and Pills", Remington's Pharmaceutical Sciences (Arthur Osol, editor), 1980; 1553–1584.

Robinson, Manford J., BSc, "Coating of Pharmaceutical Dosage Forms", Remington's Pharmaceutical Sciences, (Arthur Osol, editor), 1980; 1585–1593.

Marshall, Keith, "Solid Oral Dosage Forms", Modern Pharmaceutics, vol. 7 (Banker and Rhodes, editors), 359–427 (1979).

Hauptwerk of Beilstein, 3rd Supp., 6th vol., pp. 165, 539, 1905.

Wilson, Biochemistry, 8[1969], pp. 1042–1047, "Evidence for a Phosphoryl-Enzyme Intermediate in alkaline Phosphatase Catalyzed Reactions".

Kermici et al., J. Soc. Cosmet. Chem. 28 151–164 (1977), 1977 Society of Cosmetic Chemists of Great Britain, "Measurement of biochemical parameters in the stratum corneum".

G. Imokawa, H. Tsutsumi, Journal of the American Oil Chemists' Society, 842 (SD&C) 144), vol. 55, pp. 839–843, "Surface Activity and Cutaneous Effects of Monoalkyl Phosphate Surfactants".

Forster et al., Arch. Derm. Res. 254, 23–28 (1975) by Springer-Verlag 1975, "Subcellular Distribution of Phosphatases, Proteinases, and Ribonucleases in Normal Human Stratum Corneum and Psoriatic Scales".

Feldman, Walter, "Die Phenolyse des Trimetaphosphats. Uber das Monophenyltriphophat", Chemische Berichte Jahrg. 99, 3251–59 (translation attached).

DIPHOSPHONIC ACID ESTERS AS TARTAR CONTROL AGENTS

BACKGROUND OF THE INVENTION

Dental calculus is a deposit which forms on the surfaces of teeth at the gingival margin. A wide variety of chemical and biological agents have been suggested to retard calculus formation or to remove calculus after it is formed. Polyphosphonates have been disclosed for use as anticalculus agents. U.S. Pat. Nos. 3,678,154, issued Jul. 18, 1972; 3,737,533, issued Jun. 5, 1973; and 3,941,772, issued Mar. 2, 1976 disclose such compounds.

Dental plaque comprises an accumulation of bacteria and bacterial byproducts on teeth. Azacycloalkane-2,2-diphosphonic acids are described in U.S. Pat. No. 3,941,772, Ploger et at, issued Mar. 2, 1976 as novel compounds which are said to be useful in preparations such as mouthwashes and toothpastes in order to avoid the formation of tartar or plaque.

In spite of such work, there continues to be a need for new compounds and compositions for oral use effective for retarding calculus and/or plaque formation. In the present invention, flavorant, sweetener and/or coolant components have been attached to diphosphonic acids via an ester linkage in order to provide a tartar control agent which has improved and/or longer lasting taste and/or efficacy. Thus, one compound is provided which has two functions: improved taste; and tartar, plaque, and/or calculus control.

SUMMARY OF THE INVENTION

The present invention relates to poly (preferably di) phosphonic acid ester compounds of flavorant, coolant and/or sweetener components, said diphosphonic acid ester compounds being especially useful as tartar, plaque and/or calculus control agents having improved taste. The present invention also relates to tartar, plaque and/or calculus control compositions comprising one or more of these polyphosphonic acid ester compounds. Methods of using the compositions are also included.

DETAILED DESCRIPTION OF THE INVENTION

The subject invention relates to a compound of the formula:

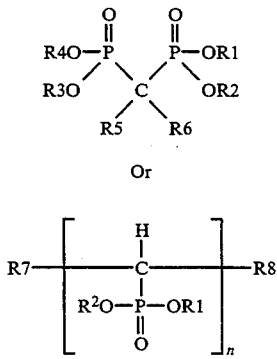

where R1 through R4 are independently selected from the group consisting of a coolant component, a sweetener component, a flavorant component; an adherent group, a physiologically active metal cation, an organic cation, and hydrogen; and at least one R1 through R4 is a coolant component, a sweetener component, or a flavorant component;

R5 is selected from the group consisting of hydrogen, alkyl containing from 1 to about 20 carbon atoms, alkenyl containing from 2 to about 20 carbon atoms, aryl (e.g., phenyl and naphthyl), phenylethenyl, benzyl, halogen (e.g. chlorine, bromine, and fluorine), amino, substituted amino (e.g. dimethyl amino, diethylamino, N-hydroxy-N-ethylamine, acetylamino),—CH2COOH, —CH2PO3H2, —CH(PO3H2)OH or—CH2CH(PO3H2)2, and salts thereof;

R6 is selected from the group consisting of hydrogen, lower alkyl, (e.g. methyl, ethyl, propyl, and butyl), amino, benzyl, halogen (e.g., chlorine, bromine, and fluorine), hydroxy,—CH2COOH, —CH2PO3H2, or CH2CH2PO3H2; and salts thereof; such as alkali metal (e.g. sodium and potassium), alkaline earth metal (e.g. calcium and magnesium), and ammonium or low molecular weight substituted ammonium (e.g., mono-, di-, and triethanolammonium) salts thereof, R7 and R8 are independently hydrogen or CH2OH; and n is an integer of from 3 to 10, preferably from 3 to 5.

Included in the above formula are linear and cyclic structures. For example, R5 can be linked to R6 to create cyclic variants. Particularly preferred is the cyclic compound where R5 is $(CH_2)_n$, where n is an integer from 3 to 5; and R6 is N-R9 wherein R9 is hydrogen or an alkyl having from 1 to 4 carbon atoms ("lower alkyl").

Mixed di (or poly) phosphonic acid esters are also included herein, such as where several R1–4 groups are flavorants, and several are coolants. The components within a category (coolants, flavorants, and sweeteners) can also vary in a single diphosphonic acid ester compound. For example, thymol may be R1 and eugenol may be R2 on the same compound.

The present invention also relates to tartar, plaque and/or calculus control compositions with good or improved taste (versus currently available antitartar or antiplaque ingredients) comprising one or more of these diphosphonic acid ester compounds.

The present invention also encompasses a method for retarding the development of plaque and/or gingivitis, tartar and/or calculus using these compositions.

Flavor-containing di or poly phosphonite acid esters herein can be synthesized by coupling flavors with hydroxy groups with di or poly phosphonic acids. Similar reactions can be conducted with coolants or sweeteners which contain hydroxy functionality.

Components

The term "coolant component" as used herein refers to coolant compounds having a hydroxy functionality which is capable of forming an ester linkage with a phosphorus(V) atom. Preferred coolant components are selected from the group consisting of 1-menthol, d-menthol, 3-1-menthoxypropane-1,2-diol ("TK-10"), menthone glycerol acetal ("MGA"), and 1-menthyl lactate.

The term "flavorant component" as used herein refers to flavorant compounds having a hydroxy functionality which is capable of forming an ester linkage with a phosphorus(V) atom. Preferred flavorant compounds are selected from the group consisting of methyl salicylate, eugenol, vanillin, thymol, cinnamaldehyde glycerol acetal ("CGA"), and linalool.

The term "sweetener component" as used herein refers to sweetener compounds having a hydroxy functionality which is capable of forming an ester linkage with a phosphorus(V) atom. Preferred sweetener components are saccharin, mannitol, sorbitol, glucose, sucrose, fructose, and neohesperidin dihydrochalcone.

The term "adherent component" as used herein refers to either monomers, oligomers, or polymers having hydroxy functionalities which are capable of forming ester linkages with phosphorus(V) atoms. The monomers, oligomers, or polymers may also possess additional hydroxy groups which may either remain unsubstituted or be linked via ester linkage to a phosphorus(V) atom which is also attached to a coolant or flavor portion. Preferred adherents are selected from the group consisting of C12-C18 diacyl glycerol, partially hydrolyzed vinyl acetate/ethylene copolymer, cellulose, chitin, glucose, glucosamine, silica gel, glycerol, and methyl vinyl ethermaleic acid.

Preferred "physiologically relevant metal cations" are sodium, potassium, calcium, zinc, copper, manganese, tin and magnesium. Most preferred are sodium and potassium.

"Organic" cation as used herein refers to cations that contain positively charged nitrogen, phosphorous, oxygen, or sulfur atoms. Such cations may contain more than one positively-charged site and, in the case of oligomers or polymers containing nitrogen, phosphorous, oxygen, or sulfur atoms, many positively-charged centers may exit. Preferred organic cations include ammonium (most preferred), protonated amines such as protonated glucosamine, and partially or fully protonated amine-containing polymers such as protonated chitosan.

Compounds

Azacycloalkane diphosphonates are diphosphonates suitable for use in the practice of this invention. Reference can be made to U.S. Pat. No. 3,941,772, to Ploger et al., Mar. 2, 1976, incorporated herein by reference, for syntheses of these materials.

In general, azacycloalkane-2,2-diphosphonates useful for substitution have the formula

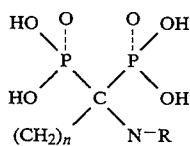

wherein R can be hydrogen or lower alkyl (C1-4), e.g., methyl, ethyl, propyl, and the like, and n is an integer from 3 to 5. Such materials are prepared by reaction of the corresponding cyclic lactam with, for example, $H_3PO_3$. In this manner are prepared, for example, azacyclopentane-2,2-diphosphonic acid ("ACP"), N-methyl-azacyclopentane-2,2-diphosphonic acid ("NMAP") and azacyloheptane-2,2-diphosphonic acid, which is more properly named as 1-azacycloheptylidene-2,2diphosphonic acid. Use of such materials as their acids or water-soluble salts, e.g., Na+, K+, NH4+, salts, is contemplated by this invention. The sodium salts of 1-azacycloheptylidene-2,2-diphosphonic acid are referred to herein, collectively, as "AHP". (It will be appreciated that, as long as the salt is water soluble, the particular salt form used herein, i.e., mono-, di-, tri- or tetra-salt, is of no particular consequence in the practice of this invention, since it is the anion that provides the anti calculus benefit.) By "effective amount" of such diphosphonates herein is meant an amount sufficient to provide an anti calculus benefit.

Other polyphosphonates found useful in the present invention are those set forth in U.S. Pat. No. 3,488,419, to McCune et at., Jan. 6, 1970 incorporated herein in its entirety by reference. Polyphosphonates useful for substitution herein are selected from the group consisting of those of the formulae:

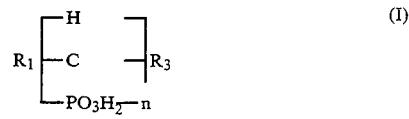

wherein R7 and R8 are hydrogen or $CH_2OH$; n is an integer of from 3 to 10; R5 is hydrogen, alkyl containing from 1 to about 20 carbon atoms, alkenyl containing from 2 to about 20 carbon atoms, aryl (e.g., phenyl and naphthyl), phenylethenyl, benzyl, halogen (e.g., dimethylamino, diethyl amino, N-hydroxy-N-ethylamino, acetyl amino), $—CH_2COOH$, $—CH_2PO_3H_2$, $—CH(PO_3H_2)$ (OH) or $—CH_2CH(PO_3H_2)_2$; R6 is hydrogen, alkyl of from 1 to 12 carbon atoms (e.g., methyl, ethyl, propyl, butyl, octyl and decyl), amino, benzyl, halogen (e.g., chlorine bromine and fluorine), hydroxyl, $—CH_2COOH$, $—CH_2PO_3H_2$, or $—CH_2CH_2PO_3H_2$; or a pharmaceutically acceptable salt thereof such as alkali metal (e.g., sodium and potassium), alkaline earth metal (e.g., calcium and magnesium), and ammonium or low molecular weight substituted ammonium (e.g., mono-, di, and triethanolammonium) nits, and a carrier suitable for use in the oral cavity, the pH of the composition being within the range from about 5.0 to about 11.0.

Operable phosphonates of the above Formula (I) include:
propane-1,2,3-triphosphonic acid;
butane-1,2,3,4-tetraphosphonic acid;
hexane-1,2,3,4,5,6-hexaphosphonic acid;
hexane-1-hydroxy-2,3,4,5,6-pentaphosphonic acid;
hexane-1,6-dihydroxy-2,3,4,5-tetraphosphonic acid;
pentane-1,2,3,4,5-pentaphosphonic acid;
heptane-1,2,3,4,5,6,7-heptaphosphonic acid;
octane-1,2,3,4,5,6,7,8-octaphosphonic acid;
nonane-1,2,3,4,5,6,7,8,9-nonaphosphonic acid;
decane-1,2,3,4,5,6,7,8,9,10-decaphosphonic acid;
and the pharmaceutically acceptable salts of these acids, e.g., sodium, potassium, calcium, magnesium, ammonium, triethanolammonium, diethanolammonium, and monoethanolammonium salts.

Among the operable polyphosphonates encompassed by the above Formula (II) are
ethane-1-hydroxy-1,1-diphosphonic acid;
methanediphosphonic acid;
methanehydroxydiphosphonic acid;
ethane-1,1,2-triphosphonic acid;
propane-1,1,3,3-tetraphosphonic acid;
ethane-2-phenyl-1,1-diphosphonic acid;
ethane-2-naphthyl-1,1-diphosphonic acid;
methanephenyldiphosphonic acid;

ethane-1-amino-1,1-diphosphonic acid;
methanedichlorodiphosphonic acid;
nonane-5,5-diphosphonic acid;
n-pentane-1,1-diphosphonic acid;
methanedifluorodiphosphonic acid;
methanedibromodiphosphonic acid;
propane-2,2-diphosphonic acid;
ethane-2-carboxy-1,1-diphosphonic acid;
propane-1-hydroxy-1,1,3-triphosphonic acid;
ethane-2-hydroxy-1,1,2-triphosphonic acid;
propane-1,3-diphenyl-2,2-diphosphonic acid;
nonane-1,1-diphosphonic acid;
decane-1-hydroxy-1,1-diphosphonic acid;
hexadecane-1,1-diphosphonic acid;
pent-4-ene-1-hydroxy-1,1-diphosphonic acid;
octadec-9-ene-1-hydroxy-1,1-diphosphonic acid;
3-phenyl-1,1-diphosphonoprop-2-ene;
octane-1,1-diphosphonic acid;
dodecane-1,1-diphosphonic acid;
phenylaminomethanediphosphonic acid;
naphthylaminomethanediphosphonic acid;
N,N-dimethylaminomethanediphosphonic acid;
N-(2-hydroxyethyl)-aminomethanediphosphonic acid;
N-acetylaminomethanediphosphonic acid;
aminomethanediphosphonic acid;
and the pharmaceutically acceptable salts of these acids, e.g., sodium, potassium, calcium, magnesium ammonium, triethanolammonium, diethanolammonium and mono-ethanolammonium salts.

Mixtures of any of the foregoing and/or their salts can be used in the compositions of this invention.

Ethane-1-hydroxy-1,1-diphosponic acid, a preferred di (or poly) phosphonate, has the molecular formula CH$_3$C(OH)(PO$_3$H$_2$)$_2$. (According to nomenclature by radicals, the acid might also be named 1-hydroxyethylidene diphosphonic acid). The most readily crystallizable salt of this acid is obtained when three of the acid hydrogens are replaced by sodium. Preferred salts for the purpose of this invention are the trisodium hydrogen salt, which has the formula:

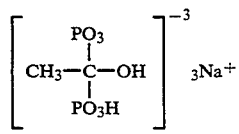

and the disodium salt.

A highly preferred diphosphonic acid ester is tetramenthyl aminohexanediphosphonate (AHP).

Without meaning to be bound by theory, it is believed that the desired coolant, sweetener or flavorant can be delivered through the action of the polyphonate derivative itself. The compositions may also provide a sustained effect by cleavage of the coolant, flavorant and or sweetener component to the molecule after cleavage of the polyphonic acid from the coolant, flavorant and/or sweetener by acid, alkaline, neutral or pyrophosphatase enzymes.

Levels

The compound of the present invention is used in the present compositions at levels of from about 0.001% to about 25%, preferably from about 0.01% to about 15%, most preferably from about 0.1% to about 5%, by weight of the composition.

Preferrably, compositions herein include from about 85% to about 99.99%, more preferably from about 90% to about 99.05%, most preferably from about 95% to about 99.5%, by weight of the composition, of carrier material.

Compositions

The present invention also encompasses an antitartar, antiplaque, or anticalculus composition, comprising, by weight of the composition, from about 0.001% to about 25%, by weight of the composition, of one or more of the present compounds.

Oral compositions herein are preferably not, in the ordinary course of usage, intentionally swallowed for purposes of systemic administration of particular therapeutic agents, but are rather retained in the oral cavity for a time sufficient to contact substantially all or most of the dental surfaces and/or oral tissues.

The phrase "a safe and effective amount", as used herein, means a sufficient amount of material to provide the desired benefit without undue adverse side effects (such as toxicity, irritation or allergic response) commensurate with a reasonable benefit/risk ratio when used in the manner of this invention. The specific safe and effective amount will vary with such factors as the particular condition that is being treated, the severity of the condition, the duration of the treatment, the physical condition of the patient, the nature of concurrent therapy (if any), and the specific formulation and optional components employed.

The compositions herein are preferably toothpaste (most preferred), mouthrinse, or liquid dentifrice. Sodium fluoride is preferably included in dentifrice compositions herein. Components to be added should be safe for oral use. By "safe" is meant without undue adverse side effects (such as toxicity, irritation or allergic response) commensurate with a reasonable benefit/risk ratio when used in the manner of this invention.

Carrier Materials

In formulating the compositions of this invention the phosphate derivative will preferably be incorporated into a carrier which may be completely inert or which may be or contain other active ingredients. The term "carrier materials", as used herein, means one or more compatible substances suitable for administration to a human or lower animal. The term "compatible", as used herein means that the components of the compositions are capable of being commingled with phosphate derivatives, actives, and with each other, in a manner such that there is no interaction which would substantially reduce the efficacy of the present compositions under ordinary use situations. Carrier materials must also be of sufficiently high purity and sufficiently low toxicity to render them suitable for administration to the human or lower animal being treated.

A wide variety of carders will be suitable depending upon the end use of the compositions. The phosphate derivatives can be incorporated into a range of topical compositions. Topical compositions include compositions applied to, or which in normal usage come in contact with, the internal membranes of the body such as those of the mouth, whether by direct or indirect application. Such compositions include (but are not limited to) dentifrices, oral rinses, lozenges, foams, and gels. Preferred compositions of the present invention are dentifrices and oral rinses.

Suitable carrier materials herein, depending on intended end use, are selected from the group consisting of solvents, suspending agents, solubilizing agents, diluents, surfactants, buffers, lubricants, thickeners, emulsifiers, flavoring agents, colorants, humectants, sweeteners, co-solvents, binders, disintegrating agents, flow-inducing agents, coolants, wetting agents, antioxidants, stabilizers, and tableting agents.

Dentifrices

Dentifrice compositions may be of the liquid, paste, powder or gel type. These compositions will usually comprise a finely divided abrasive or polishing material, e.g. precipitated chalk, silica, magnesium silicate, calcium polymetaphosphate, aluminum hydroxide or other similar materials well known in the art. Abrasive materials are more fully described in U.S. Pat. No. 3,070,510, Cooley et at., Dec. 25, 1962, which is incorporated herein by reference. Toothpaste compositions additionally contain a surfactant or foaming agent. Suitable surfactants are those which are reasonably stable and foam throughout a wide pH range, including non-soap anionic, nonionic, cationic, zwitterionic and amphoteric organic synthetic detergents. These surfactants are disclosed by Gieske et at. in U.S. Pat. No. 4,051,234, issued Sep. 27, 1977, also incorporated herein by reference.

Optional ingredients in dentifrice compositions include flavoring agents, colorants, buffers, lubricants, thickeners, emulsifiers or plasticizers, and humectants. Dentifrice carder materials typically comprise from about 50% to about 94%, and preferably from about 60% to about 80%, by weight of the dentifrice compositions.

Oral Rinses

Oral rinses usually comprise an aqueous, alcoholic, or aqueous-alcoholic solution of an antiseptic which is often colored or flavored for palatability. Optional ingredients include humectants, surfactants, sweeteners, emulsifying agents, fluoride ion sources, tartar control and anti-plaque agents. Oral rinse products may also be formed by dissolving a powder or tablet containing stannous gluconate in water just prior to use.

Conventional oral rinse compositions generally comprise from about 0% to 60% ethyl alcohol, 0% to 20% of a humectant, 0% to 2% emulsifying agents, 0% to 0.5% sweetening agents, 0% to 0.3% flavoring agents and the balance water.

Although water itself may make up the entire carder, typical oral formulations also contain a co-solvent including but not limited to alcohol, propylene glycol, glycerin, sorbitol solution, and the like, to assist solubilization and incorporation of water-insoluble ingredients, flavoring oils and the like into the composition. In general, the compositions preferably contain from about 5 to about 25 volume/volume percent of the co-solvent, most preferably from about 10 to about 20 volume/volume percent of the co-solvent.

Oral compositions herein are preferably toothpaste (most preferred), mouthrinse, or liquid dentifrice. Sodium fluoride is preferably included in dentifrice compositions herein. Components to be added should be safe for oral use.

Other Carriers

Coolant materials may also be included as carder materials in the invention compositions. Preferred coolants in the present compositions are the paramenthane carboxyamide agents such as N-ethyl-p-menthane-3-carboxamide (known commercially as "WS-3"), and 3-1-menthoxypropane-1,2-diol (known commercially as "TK-10"), and mixtures thereof. These coolants are described in PCT Patent Application Publication WO 92-17164, to Upson et at., published Oct. 15, 1992. TK-10 is also described in U.S. Pat. No. 4,459,425 to Amano et at., issued Jul. 10, 1984; and WS-3 and the paramenthane carboxyamide agents are also described in U.S. Pat. No. 4,136,163 to Watson et at., issued Jan. 23, 1979. The disclosures of all three of these patent publications are incorporated by reference herein in their entirety.

Active

The invention compositions may also contain a safe and effective mount of one or more additional actives. Some additional actives that are useful in these compositions include (but are not limited to) antimicrobial agents such as bisbiguanides or phenolics; antibiotics such as metronidazole, or clindamycin; dentinal desensitizing agents such as potassium nitrate, strontium chloride or sodium fluoride; odor masking agents such as peppermint oil or chlorophyll; local anesthetic agents such as lidocaine or benzocaine; antioxidants such as thymol, alphatocopherol and butylated hydroxy toluene; lipopolysaccharide complexing agents such as polymyxin; quaternary ammonium compounds such as benzalkonium chloride and cetyl pyridinium chloride; aromatics such as camphor, eucalyptus oil, and aldehyde derivatives such as benzaldehyde; denture adhesives such as lower alkyl vinyl ethermaleic acid or anhydride copolymers and their salts; coolants having therapeutic efficacy such as menthol; or peroxides such as urea peroxide.

Preferred formulations for the present compositions are dental care preparations such as dentifrices and oral rinses. Dental care preparations may comprise a soluble fluoride ion source as one of the actives. The soluble fluoride ion source is used in an amount sufficient to provide from about 10 to about 5000 ppm of the fluoride ion. Preferred fluorides are sodium fluoride, stannous fluoride, inidium fluoride, and sodium monofluorophosphate. Norris et at., U.S. Pat. No. 2,946735, issued Jul. 26, 1960 and Widder et al., U.S. Pat. No. 3,678,154, issued Jul. 18, 1972, disclose such salts as well as others. Both patents are incorporated herein by reference in their entirety.

Various polymers and mixtures thereof are also useful in dental care preparations. These polymers may be synthetic anionic polymeric polycarboxylates and their complexes and/or carboxyvinyl polymers. Polymers useful in the present compositions are disclosed in U.S. Pat. No. 4,906,456 to Gaffer et al., issued Mar. 6, 1990, incorporated herein by reference in its entirety.

Pyrophosphate salts are pharmaceutical actives that may also be included in dental care preparations. Any of the alkali metal pyrophosphate salts may be used in either their hydrated or unhydrated forms. Pyrophosphate salts are described in more detail in Kirk & Othmer, Encyclopedia of Chemical Technology, Second Edition, Volume 15, Interscience Publishers (1968), incorporated herein by reference in its entirety.

Additional anti-plaque and anti-gingivitis pharmaceutical actives may also be included in the dental preparations. These actives include quaternary ammonium compounds or bis-biguanides. Oral compositions comprising stannous ion are described fully in U.S. Pat. No.

5,004,597 to Majeti et al., issued Apr. 2, 1991, incorporated herein by reference in its entirety. Disinfectant agents like triclosan and antiseptic agents like thymol may also be included in the dental preparations.

Methods

Included is a method comprising contacting dental enamel surfaces with an effective mount of a composition according to the above to reduce or prevent calculus or gingivitis, or tartar or plaque.

All percentages and ratios used herein are by weight, and all measurements are made at 25° C., unless otherwise specified.

The following examples further describe and demonstrate embodiments within the scope of the present invention. These examples are given solely for the purpose of illustration and are not to be construed as limitations of the present invention as many variations thereof are possible without departing from the spirit and scope of the present invention.

Example I

Toothpaste Composition

A toothpaste composition according to the present invention is prepared having the following components:

| Component | Weight % |
|---|---|
| Tetramenthyl AHP | 1.5 |
| Purified Water | Balance |
| Sorbitol | 60.565 |
| Sodium Fluoride (1100 ppm F$^-$) | 0.243 |
| Saccharin | 0.130 |
| Colorant | 0.500 |
| Silica | 20.000 |
| Flavor | 0.500 |
| Carboxymethyl cellulose | 0.300 |
| Xanthan Gum | 0.475 |
| Trisodium Phosphate | 1.450 |
| Monosodium Phosphate | 0.590 |
| Sodium Alkyl Sulfate Solution (27.9% in H2O) | 4.000 |
| Titanium Dioxide | 0.525 |

*= tetramenthyl aminohexanediphosphonate

Add sorbitol to water and mix. Dissolve salts, tetramenthyl AHP, sodium fluoride, saccharin, trisodium phosphate, and monosodium phosphate. Adjust the pH to 7.0 and then add colorant. Separately combine silica, carboxymethyl cellulose, and xanthan gum and then slowly add this mixture to the composition while mixing continuously. Add sodium alkyl sulfate. Add the flavor (eg, spearmint, peppermint, wintergreen, fruit) to the composition and mix for ten more minutes.

Other compounds of the present invention can be substituted for the tetramenthyl AHP, such as tetramenthyl 1-hydroxyethylidene diphosphonate ("EHDP"). The amount employed in the composition can vary within the limits described herein.

Example II

Oral Mouth Rinse Composition

An oral mouth rinse composition according to the present invention is prepared having the following components:

| Component | Weight % |
|---|---|
| Tetramenthyl EHDP* | 0.5 |
| Ethanol (190 proof) | 16.250 |
| Polysorbate 80 | 0.120 |
| Glycerin | 10.000 |
| Purified Water | Balance |
| Benzoic Acid | 0.0045 |
| Cetylpyridinium Chloride | 0.045 |
| Domiphen Bromide | 0.005 |
| Sodium Saccharin | 0.060 |
| Colorant | 0.040 |
| Sodium Benzoate | 0.0537 |

*= tetramenthyl 1-hydroxyethylidene diphosphonate

To ethanol, add all ingredients except tetramenthyl EHDP and mix for 5 minutes. Add tetramenthyl EHDP first and then adjust the pH of the composition to pH 6.0.

Other compounds of the present invention can be substituted for the tetramenthyl EHDP such as tetramenthyl AHP. The amount of the diphosphonate employed in the composition can vary within the limits described herein.

Preparation of Tetramenthyl AHP

The following is a method for synthesizing Tetramenthyl Azacycloheptane-2,2-diphosphonate (Tetramenthyl AHP).

Step 1. Preparation of Azacycloheptane-2,2-diphosphonic Acid Chloride:

Add azacycloheptane-2,2-diphosphonic acid (32.4g, 0.125 mol) to oxalyl chloride (400g, 3.2 mol) portionwise so as to allow gas to be evolved at a moderate rate and maintain the temperature at about 30° C. Warm the mixture for 30 minutes at 35° C. once gas production ceases and then concentrate it under vacuum at 50° C. Repeatedly add methylene chloride (3×50 mL) to the remaining liquid and remove it under vacuum. Use the crude azacycloheptane-2,2-diphosphonic acid chloride so obtained directly in the next step.

Step 2. Reaction with 1-Menthol:

Add a solution of azacyloheptane-2,2-diphosphonic acid chloride (33.3 g, 0.1 mol) in 50 mL of methylene chloride dropwise to a stirred, ice cooled solution of 1-menthol (68.8 g, 0.44 mol) and triethylamine (61.3 mL, 0.44 mol) in 100 mL of methylene chloride. Once the addition is complete, heat the mixture at reflux for 2 hours. Cool the solution to room temperature and wash it, first with a 5% aqueous solution of hydrochloric acid (3×50 mL) and then with water (2×50 mL). Dry the solution over sodium sulfate and remove the solvent under vacuum.

Preparation of Tetramenthyl EHDP

The following is a method for synthesizing 1-Hydroxyethylidenediphosphonate (Tetramenthyl EHDP).

Step 1. Preparation of Dimenthyl Acetylphosphonate:

React 1-menthol and methyldichlorophosphite to give methyldimenthylphosphite (MDP). Add MDP (186.3 g, 0.5 mol) dropwise with stirring to acetyl chloride (39.2 g, 0.5 mol) over a period of about 30 minutes while maintaining the temperature of the reaction mixture below 30° C. by cooling in an ice-bath. After the addition is complete, stir the mixture at 25° C. for 1 hour and then heat it gently on a steam bath until the evolution of methyl chloride ceases. Use the crude dimenthylacetylphosphonate obtained directly in the next step.

Step 2. Coupling with Dimenthylhydrogenphosphite:

Mix dimenthylhydrogenphosphite (35.9 g, 0.1 mol) and diethylamine (7.3 g, 0.1 mol) in a round-bottom flask and add dimenthyl acetylphosphonate (40 g, 0.1 mol) dropwise with stirring. Stir the mixture for 2 hours and then partition it between water and diethyl ether. After washing the ether layer with a 5% aqueous solution of hydrochloric acid, dry it over sodium sulfate and remove the ether under reduced pressure. Triturate the product with n-hexane.

What is claimed is:

1. A compound of the formula

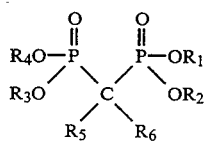

where at least one of R1 through R4 is 1-menthol or d-menthol;

R5 is selected from the group consisting of an alkyl containing 1 carbon and $(CH_2)_n$ where n is an integer from 3 to 5; and R6 is selected from the group consisting of hydrogen, lower alkyl, amino, benzyl, halogen, hydroxy, —CH2COOH, —CH2PO3H2, or CH2CH2PO3H2; and salts thereof.

2. The compound of claim 1 where R5 and R6 are linked as cyclic, and R5 is $(CH_2)_n$, where n is an integer from 3 to 5; and R6 is N-R7 wherein R7 is hydrogen or an alkyl having from 1 to 4 carbon atom.

3. An antitartar or antiplaque or anticalculus composition, comprising, by weight of the composition, from about 0.001% to about 25%, by weight of the composition, of one or more compounds according to claim 1.

4. The composition of claim 3 in the form of a dentifrice or mouthrinse.

5. The composition of claim 3 in the form of a toothpaste or mouthrinse.

6. A method comprising contacting dental enamel surfaces with an effective mount of a composition according to claim 3 to reduce or prevent calculus or gingivitis, or tartar or plaque.

* * * * *